(12) United States Patent
Bargoot et al.

(10) Patent No.: US 6,750,039 B1
(45) Date of Patent: Jun. 15, 2004

(54) FILTRATION APPARATUS AND METHOD FOR THE SEPARATION OF MICROSCOPIC ENTITIES FROM A FLUID

(75) Inventors: Frederick G. Bargoot, Wellesley, MA (US); Jens J. Hyldig-Nielsen, Holliston, MA (US); Donald B. Rising, Stow, MA (US); Henrik Stender, Waltham, MA (US)

(73) Assignee: Boston Probes, Inc., Bedford, MA (US)

( * ) Notice: Subject to any disclaimer, the term of this patent is extended or adjusted under 35 U.S.C. 154(b) by 168 days.

(21) Appl. No.: 10/101,026

(22) Filed: Mar. 19, 2002

Related U.S. Application Data (60) Provisional application No. 60/277,698, filed on Mar. 21, 2001.

(51) Int. Cl.[7] .............................. C12Q 1/04; C12M 1/00; C12M 1/36
(52) U.S. Cl. .................. 435/34; 435/283.1; 435/286.5; 422/68.1
(58) Field of Search ............... 435/34, 283.1, 435/286.5; 422/68.1

(56) References Cited

U.S. PATENT DOCUMENTS

| | | | |
|---|---|---|---|
| 4,036,698 A | 7/1977 | Bush et al. ............... 195/103.5 |
| 4,124,449 A | * 11/1978 | Barta et al. ................. 195/139 |
| 4,317,726 A | 3/1982 | Shepel ........................ 210/236 |
| 4,444,661 A | 4/1984 | Jackson et al. ............. 210/446 |
| 4,614,585 A | 9/1986 | Mehra et al. ............. 210/433.2 |
| 4,777,137 A | 10/1988 | Lemonnier .................. 435/299 |
| 4,790,640 A | 12/1988 | Nason ......................... 350/534 |
| 4,829,005 A | 5/1989 | Friedman et al. ........... 435/296 |
| 4,849,330 A | 7/1989 | Humphries et al. ............. 435/4 |
| 4,912,037 A | 3/1990 | Lemonnier .................... 435/34 |
| 4,974,952 A | 12/1990 | Focht .......................... 350/536 |
| 5,112,488 A | 5/1992 | Lemonnier .................. 210/541 |
| 5,202,262 A | 4/1993 | Lemonnier .................. 435/299 |
| 5,252,293 A | 10/1993 | Drbal et al. ................. 422/101 |
| 5,288,638 A | 2/1994 | Lemonnier .................. 435/299 |
| 5,409,832 A | 4/1995 | Pocock ........................ 435/287 |
| 5,417,576 A | 5/1995 | Hill ............................. 435/299 |
| 5,429,742 A | 7/1995 | Gutman et al. ........ 210/321.75 |
| 5,486,335 A | * 1/1996 | Wilding et al. ................ 422/55 |
| 5,624,554 A | 4/1997 | Faulkner et al. ............ 210/232 |
| 5,851,390 A | 12/1998 | Lemonnier ............... 210/321.1 |
| 5,891,394 A | 4/1999 | Drocourt et al. .............. 422/50 |

OTHER PUBLICATIONS

Stender, H. et al, Fluorescence In Situ Hybridization Assay Using Peptide Nucleic Acid Probes For Differentiation Between Tuberculous And Nontuberculous Mycobacterium Species In Smears Of Mycobacterium Cultures. *Journal of Clin. Microb.*, 37, 2760–2765 (1999).

* cited by examiner

*Primary Examiner*—Louise N. Leary
(74) *Attorney, Agent, or Firm*—Richard J. Birch (57) ABSTRACT

This invention relates to a filtration apparatus and method for the separation of microscopic entities from a fluid (liquid or gas) and subsequent visual or imaging microscopic analysis of the entities separated thereon either directly or after treatment of the entities whilst on the apparatus in order to enhance their subsequent visualization and/or imaging. Such treatment can comprise reaction with reagents contained in other solutions that can be made to imbibe and/or pass through the filtration apparatus and which can be washed with solutions that can be made to imbibe and/or pass through the filtration apparatus. An example of a specific area of application is in the microbiological testing of fluids in order to detect, identify and/or enumerate microorganisms contained in a fluid test sample.

36 Claims, 11 Drawing Sheets

Fig. 11b
Filter Slide, Circular Format

Fig. 11a
Filter Slide, Generally Elliptical Format

FILTRATION APPARATUS AND METHOD FOR THE SEPARATION OF MICROSCOPIC ENTITIES FROM A FLUID

CROSS REFERENCE TO RELATED APPLICATIONS

This application claims the benefit of U.S. Provisional Application No. 60/277,698 filed on Mar. 21, 2001.

FIELD OF THE INVENTION

This invention relates to a filtration apparatus and method for the separation of microscopic entities from a fluid (liquid or gas) and subsequent visual or imaging microscopic analysis of the entities separated thereon either directly or after treatment of the entities whilst on the apparatus in order to enhance their subsequent visualization and/or imaging. Such treatment can comprise reaction with reagents contained in other solutions that can be made to imbibe and/or pass through the filtration apparatus and which can be washed with solutions that can be made to imbibe and/or pass through the filtration apparatus. An example of a specific area of application is in the microbiological testing of fluids in order to detect, identify and/or enumerate microorganisms contained in a fluid test sample.

This invention also relates to an apparatus upon which organic and/or biological molecules (or organisms) can be immobilized and reacted with reagents contained in other solutions that can be made to imbibe and/or pass through the filtration apparatus and which can be washed with solutions that can be made to imbibe and/or pass through the filtration apparatus. An example of a specific area of application is in the immobilization of a probe or probes onto the apparatus for the purpose of capturing, from a test solution, nucleic acids containing a specific nucleotide sequence represented by the complement to the nucleic acid or non-nucleic acid (e.g. Peptide Nucleic Acid) probe or probes immobilized onto the apparatus.

BACKGROUND OF THE INVENTION

One area of application pertains to the microbiological testing of fluids with the goal of detecting, identifying, and/or enumerating microorganisms contained in a test fluid, or defined volume of test fluid.

Traditionally, a sample suspected of containing contaminating bacteria, yeast, or other microorganism of interest, is filtered through a sterile, microporous membrane (typically 0.22 $\mu$ or 0.45 $\mu$porosity). The membrane is then exposed to a selective growth medium (e.g. agar or broth-based) and incubated, usually at 37° C., until visible colonies appear on the membrane; usually 24–72 hours, depending on the species of microorganism. Incubation for a shorter time results in microscopic colonies that can very tediously be counted under a high power microscope objective. This process however, requires substantial technician time and is subject to significant counting error. When subjected to longer incubation, the visible colonies are manually counted without the use of a microscope and the original concentration of microorganisms can be calculated. Many apparati have been developed for this purpose (e.g. U.S. Pat. No. 4,317,726, U.S. Pat. No. 4,614,585, U.S. Pat. No. 4,777,137, U.S. Pat. No. 4,912,037, U.S. Pat. No. 5,202,262, U.S. Pat. No. 5,288,638, U.S. Pat. No. 4,036,698, U.S. Pat. No. 4,829,005, U.S. Pat. No. 5,409,832, U.S. Pat. No. 5,112,488, all of which are herein incorporated by reference). All of these are intended for the manual counting of colonies as described above.

A considerable amount of time can be saved if the incubation time is reduced to 4–6 hours and counting of the microscopic colonies is automated. Such a method for identification and enumeration of microorganisms has been developed and is termed Fluorescence In-Situ Hybridization (FISH) followed by automated image capture and analysis using an automated commercially available laser or charge coupled device (CCD)-based imaging system (Stender, et. al., J. Micro. Meth. 1449, 2001). This FISH method typically involves the following steps:

1. Filtration through a microporous membrane, trapping microorganisms on the membrane filter. The filter is part of a filtration apparatus with a fluid reservoir on one side and a waste receptacle on the other. Pressure can be applied to the reservoir or vacuum can be applied to the waste side in order to force the fluid through the membrane to the waste side, trapping any microorganisms on or within the filter.
2. Growth of the microorganisms on the filter by transferring the filter from the filtration apparatus to a cellulose pad or agar plug imbibed with a selective growth medium.
3. Fixation of the microorganisms on the filter with a fixative solution by transferring the filter from the growth medium to a cellulose pad imbibed with a fixative solution.
4. Hybridization on the filter with a Peptide Nucleic Acid (PNA) probe specific to the microorganism in question. The probe is labeled with a fluorescent molecule. The filter is transferred from the fixation medium to a glass slide, microorganism side up. A small amount of hybridization solution is pipetted onto the top of the membrane filter and a cover slip placed thereon in order to spread the hybridization solution over the membrane and minimize evaporation. The filter on the slide is incubated at an elevated temperature (45–65° C.) in a humidified chamber.
5. Washing excess and unbound reagent from the filter. The slide with the filter is placed in a standard slide tray and incubated in heated wash solution. The membrane is gently teased from the slide in order to wash both sides of the membrane and remove as much hybridization solution as possible.
6. Transferring the membrane to an imager for analysis. The membrane is removed from the wash solution and placed on a microscope slide for subsequent imaging and analysis.

This process involves manually handling the delicate microporous filter directly multiple times prior to the analysis step, increasing the chance of contamination and damage.

In addition to the analysis of microorganisms or particles, this invention also pertains to microarrays. Microarrays is a fast growing field that allows for deposition of ~100–200 micron spots of target molecules (in most cases, nucleic acid probes, antigens, or antibodies) that are immobilized onto a support substrate, which in most cases is a pretreated glass microscope slide. The spots are arrayed in a rectangular matrix on the surface of the slide allowing for thousands of experiments per slide. Reagents are flowed over the surface or the slides are immersed in reagent and rinse reservoirs utilizing standard equipment used for processing glass microscope slides in fields such as histochemistry, cytochemistry, immunohistochemistry, and cytogenetics. Recently, (solid) glass slides coated on one surface with a microporous matrix have become commercially available. The microporous matrix (for example, nitrocellulose, nylon)

purportedly provides more surface area for immobilization and reaction with target molecules resulting in localized fluorescent, chemiluminescent, or radioactive product as an indicator that a target molecule has bound to the probe immobilized within a given "spot".

Discussion of Certain Documents

U.S. Pat. No. 5,891,394 discusses an apparatus for detection and enumeration, but not identification, of microorganisms on a filter by fluorescence. Their fluorescence method is not capable of identifying a specific microorganism in the presence of other microorganisms. Furthermore, filtration and processing are done on standard 25 mm membranes. After processing, the filter is manually transferred to a well in the apparatus for analysis. There is no slide involved and the membrane is directly handled multiple times prior to analysis.

U.S. Pat. No. 4,124,449 describes a filter holder for mounting on the stage of a microscope. This apparatus allows for filtration of fluids through an integral microporous membrane, incubation of microorganisms retained on the filter with a dye to stain them, and visualization under a light or dark field microscope for the visual enumeration of microorganisms. It is not only restricted to visual observation with a microscope, but its overall dimensions far exceed those of a standard microscope slide, rendering it incompatible with standard apparatus for processing specimens on a microscope slide.

U.S. Pat. No. 5,252,293 describes a plastic disposable analytical slide with an integral microporous filter membrane. The plastic slide portion contains a number of physical features, such as slits and indentations, that allow it to align the filter in an apparatus (U.S. Pat. No. 5,529,752) designed for deposition of ligands onto specific spots on the membrane, and expose these spots to hapten-containing solutions. The slide is then moved to a measuring module within the apparatus where other features on the slide cause it to align with a measuring apparatus to quantify the amount of hapten bound. This analytical slide is for a specific application and compatible only with the apparatus of U.S. Pat. No. 5,529,752 and does not have the general applicability of the current invention, that being suitable for use in any microscope slide format.

U.S. Pat. No. 5,851,390 describes a filter membrane and housing with an elliptical shape. The elliptical shape of the assembly makes it easier to handle, particularly to attach a syringe via a luer attachment, reduces membrane waste in the manufacturing process, and facilitates addition of hydrophobic areas during the manufacturing process. The intended use is to filter entities from a fluid sample and retain the filtrate for subsequent use. The filter with its housing are discarded. The apparatus can be produced in different sizes, depending on the application, and the size of the filtration area is not restricted.

DESCRIPTION OF THE INVENTION

In one embodiment, the current invention pertains to a microporous filter membrane incorporated into a support having overall dimensions of a microscope slide such that the unit (Filter Slide) can be handled, viewed, stored, and otherwise processed as is any microscope slide. In another embodiment, the present invention pertains to peripheral apparati that mate with the Filter Slide providing a uniform way to filter fluids and process particles (including microorganisms) retained on the membrane of the Filter Slide.

When used with the appropriate mating apparati described herein, the current invention can be used to filter fluids through the membrane portion and retain any microscopic particles or microorganisms contained therein on one surface or trapped within the matrix of the membrane. Before and/or after observation or imaging of these entities, they can be treated with reagents that react with the retained particles or microorganisms such as to enhance their visualization. For example, the retained particles or microorganisms can be exposed to these reagents by causing the reagents to pass through the membrane with applied vacuum or pressure, or by exposing one side or the other of the membrane with a reagent and relying on diffusion to imbibe the reagent into the interstices of the membrane and thus to contact and react with the particles (including microorganisms) retained therein. These post-binding reactions usually result in a product that is fluorescent, colored, or chemiluminescent and can be imaged in any number of commercially available imaging instruments such as for example a laser based array scanner (available from suppliers such as Affymetrix, Inc., Bedford, Mass., and Axon Instruments, Inc., Foster City, Calif.) or a CCD camera equipped imaging devices (available from Applied Precision, Inc., Issaquah, Wash.)

It is an advantage of the present invention that once an image is captured, the particles or colonies of microorganisms can be counted and/or analyzed using commercially available image processing software (such as available from Media Cybernetics, Inc., Silver Spring, Md.). The further advantage is that this counting and/or analysis can be accomplished in a matter of seconds with a high degree of accuracy. Taken together these advances substantially reduce the cost and labor content of the analysis process as well as expedite the result and improve accuracy, reliability and reproducibility.

The current invention incorporates the filter membrane directly into the microscope slide dimensions. The slide, not the filter, is directly manipulated throughout any processing steps. After processing, the filter is ready for analysis without transfer to a glass slide, thus eliminating a time-consuming step and minimizing the risk of damage to the membrane. Furthermore, the invention is compatible with any visualization apparatus that accepts standard glass microscope slides and requires no additional features or special fixturing for alignment.

The current invention can be practiced with a variety of membranes, with the advantage that reagents can be brought into contact with the membrane from either side, or they can be drawn through the membrane, providing for more complete reaction and rinsing between reagent steps while still being in the format of a standard microscope slide. The flow through capability of the current invention makes it easier to automate the sample processing steps. Handling by the user is the same as with the microscope slide-based arrays they currently use.

The current invention integrates and simplifies the FISH process as described above and provides a uniform and robust way to handle and process the microorganisms retained on the filter membrane.

DESCRIPTION OF THE DRAWINGS

FIG. 6a Top cap for generally elliptical filter format, top view

FIG. 6b Top cap for generally elliptical filter format, bottom view

DRAWING CALLOUT REFERENCES

Description

Figure 4:
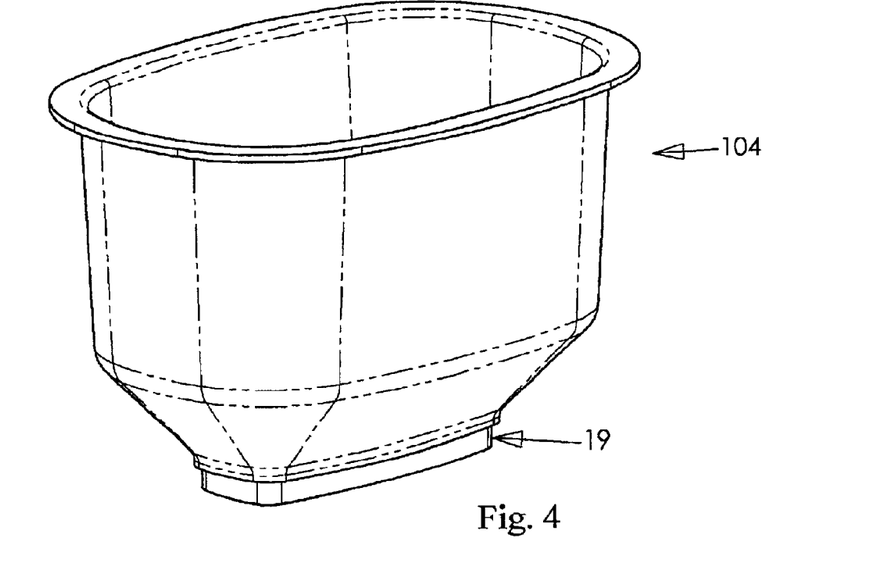
FIG. 4 Funnel for generally elliptical filter format
Figure 6A:
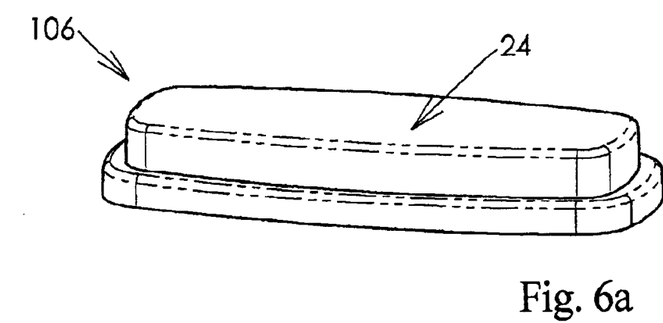
Figure 6B:
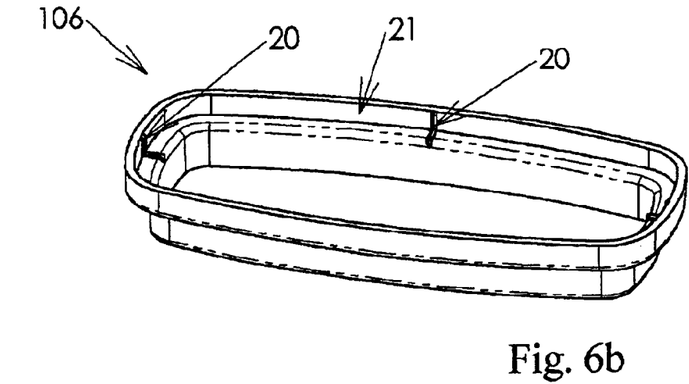

Feature Callout
1 Plastic slide for circular filter
2 Plastic slide for generally elliptical filter
3 Thru hold for mounting filter
4 Filter, mounted to plastic support
5 Solid, reusable support
6 Aperture through the solid support
7 Filter membrane
8 Plastic base
9 Disposable filter module.
10 First member of Slide holder
11 Second member of Slide holder
12 Living Hinge
13 Rear wall of second member
14 Through aperture of second member of Slide Holder
15 Spring Lock on second member
16 Latch on first member
17 Through aperture in first member of Slide Holder
18 Inner mating wall of aperture 17
19 Outer mating wall of funnel, FIG. 4.
20 Ribs on inner wall of top cap, FIG. 6b
21 Inner wall of top cap
22 Feet on the circular format top cap
23 Cap portion of the circular format top cap
24 Top surface of the top cap
25 Outer mating wall of aperture 17
26 Deep cavity in Reagent Applicator 108
27 Shelf or shallow cavity in Reagent Applicator 108
28 Top surface of Reagent Applicator 108
29 Location button for disposable filter module 9
30 Thru hole in solid, reusable support 5 for location button 29.
35 Protruding end of filter slide assembly
36 Locking Rails, Slide Holder with no latches
37 End Flange, Slide Holder Clamp
38 Sealing Gasket
39 Upstream side of filter for filtration
100 Filter Slide assembly with Circular aperture
101 Filter Slide assembly with Generally elliptical aperture
102 Filter Slide assembly with reusable slide support and disposable filter module
103 Slide holder for generally elliptical format
104 Funnel to fit Slide Holder
105 Vaccuum manifold adapter to fit Slide Holder
106 Top Cap for generally elliptical format
107 Top Cap for circular format
108 Reagent Applicator for generally elliptical format, agar or cellulose pad
109 Reagent Applicator for circular format, agar or cellulose pad
110 Slide holder for Circular format
111 Slide holder, Circular format, no latches.
112 Slide holder clamp
113 Filtration Unit combining slide holder and slide holder clamp.
114 Filtration Unit cross section combining filter slide, slide holder, slide holder clamp, and sealing gasket.

DESCRIPTION OF PREFERRED EMBODIMENTS

Microscope slides are designed to fit onto the stage of a microscope or imaging apparatus and take on many forms. Most common surface areas measure nominally 25 mm×75 mm, 1"×3", 26 mm×75 mm, and 2"×2". Most common thicknesses are nominally 1 mm and 1.2 mm. The current invention includes, but is not restricted, to these sizes. For the purpose of illustration only, examples that follow will be described for the 25 mm×75 mm×1.2 mm format.

Microporous membranes are available in many sizes and pore sizes from many commercial sources (e.g. Millipore Corporation, Bedford, Mass.; Pall Corporation, East Hills, N.Y.). They can be made of materials such as, but not restricted to, nitrocellulose and cellulose, and organic polymers such as nylon, polytetrafluoroethylene (PTFE), and polyvinylidenedifluoride (PVDF). These membranes can also be made of ceramic materials or metals such as sintered aluminum. This invention contemplates that said microporous membranes can be coated or otherwise treated for optimal performance in certain applications. For example, Millipore Corporation provides numerous commercially available and polyvinylidiene fluoride (PVDF) membranes that have been coated to thereby prepare membranes that exhibit hydrophilic properties from these hydrophobic base materials.

The filterable area of the membrane can take on many shapes consistent with the microscope slide area. Loose, microporous laboratory filters are commercially available in many sizes, particularly 25 mm (15 mm diameter filterable area) and 47 mm (37 mm diameter filterable area) diameters which are commonly used to filter samples of up to a few hundred milliliters. Examples of two alternatives are described herein: one with a circular filtration area that approximates the filterable area of commercial 25 mm diameter filters, and one with a generally elliptical area that maximizes the filtration area consistent with the 25×75 mm microscope slide format while maintaining structural integrity for the plastic molded version of the invention and that has approximately 75% of the filterable area of a standard 47 mm diameter filter.

Figures 1A, 1B:
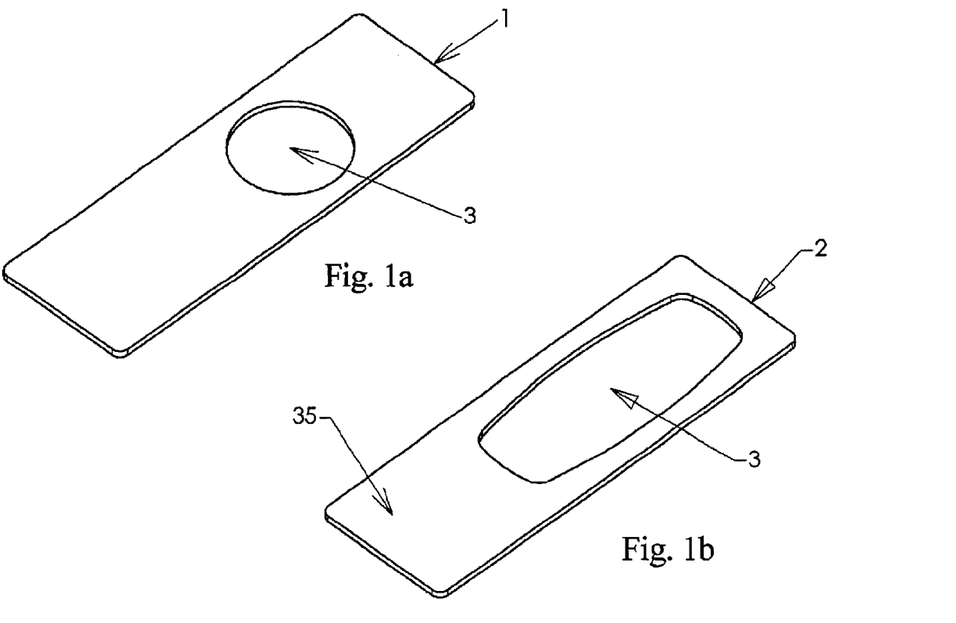
FIG. 1a Slide support for circular membrane format
FIG. 1b Slide support for generally elliptical membrane formats.
Figure 1C:
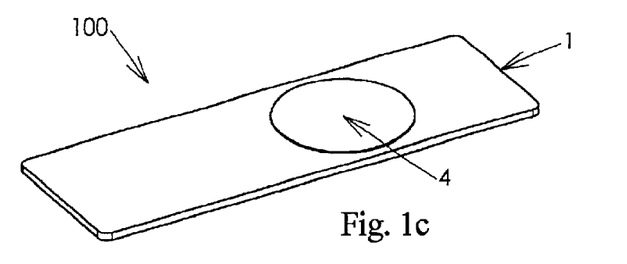
FIG. 1c Filter slide, circular format
Figure 1D:
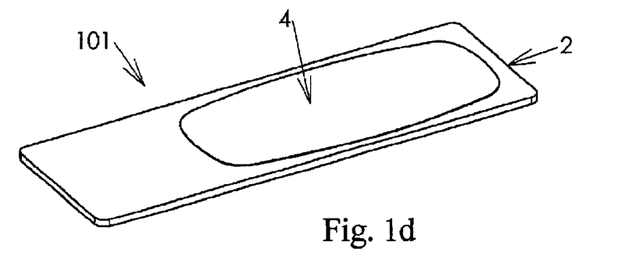
FIG. 1d Filter slide, generally elliptical format

The slide support can be fabricated or molded from a plastic material such as polystyrene, polymethylmethacrylate, or polycarbonate. The slide support for the circular (1) and generally elliptical (SE) (2) formats are shown in FIG. 1a and FIG. 1b, respectively. The microporous membrane can be aligned with the aperture and fixed to the slide support by a variety of methods including ultrasonic welding, solvent bonding, or insert molding. In this case, the entire part can be archived or disposed of. The slide support with filter adhered to it (4) is shown in FIG. 1c and FIG. 1d for the circular (100) and SE (101) formats, respectively.

Figure 2A:
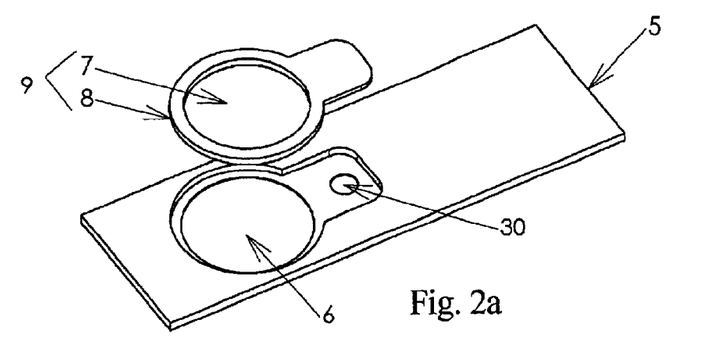
FIG. 2a Reusable slide support with disposable filter riodule, exploded top view FIG. 2b Reusable slide support with disposable filter module, exploded bottom view FIG. 2c Reusable slide support with disposable filter module assembly, top view FIG. 3a Slide holder with integral latch mechanism, partially closed FIG. 3b Slide holder with integral latch mechanism, fully opened, interior view FIG. 3c Slide holder with integral latch mechanism, fully opened, exterior view FIG. 3d Slide holder, no integral latch FIG. 3e Slide Holder Clamp FIG. 3f Assembly combining slide holder and slide holder clamp.
Figure 2B:
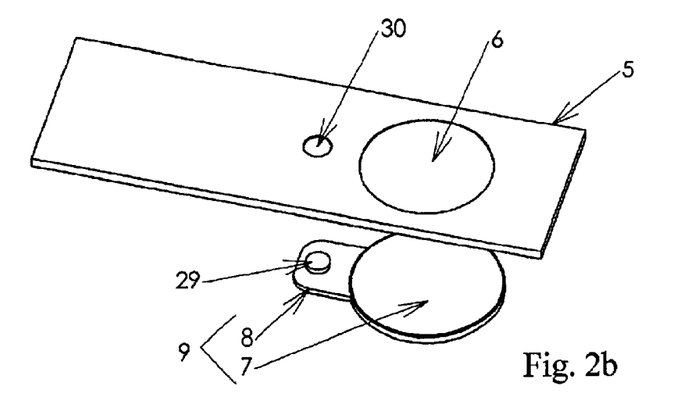
Figure 2C:
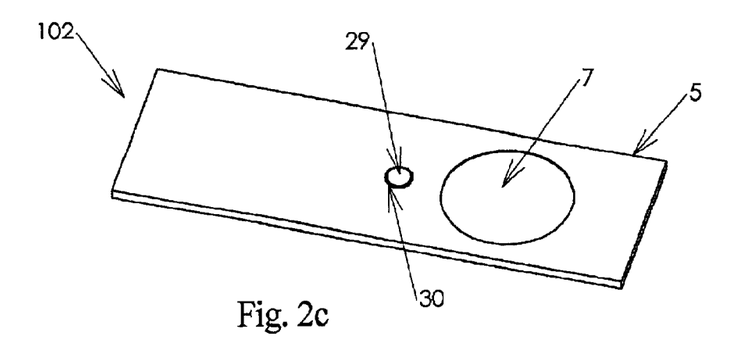

An alternative embodiment (FIG. 2a–c) for the support (5) is fabricated from a solid, reusable material such as stainless steel, with an aperture (6) created therein that accepts the filter (7) adhered to a plastic base (8) yielding a disposable filter module (9). The filter module snaps into and is retained by the support (5) while simultaneously fixing the membrane (6) parallel to the plane of the support and retaining the filter module within the microscope slide dimensions. FIG. 2a and FIG. 2b show exploded views from the bottom and top, respectively. FIG. 2c shows the assembled Filter Slide (102) from the top.

The invention is further illustrated using the generally elliptical format, understanding that the circular or other formats can be applied as well and are included. Further, the example below illustrates the use for growth, identification, and enumeration of microorganisms. Any filterable product can be used and reacted with any set of reagents and are included as part of this application.

Figure 3A:
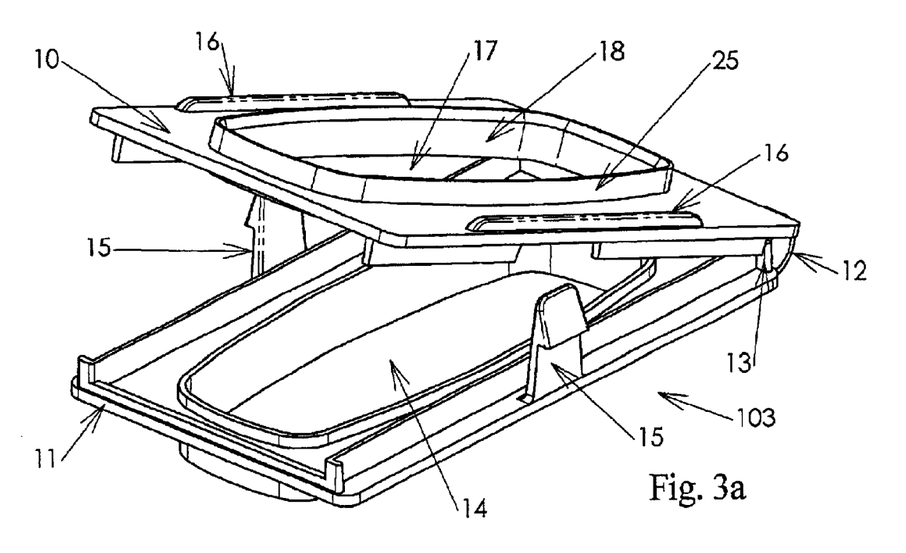
Figure 3B:
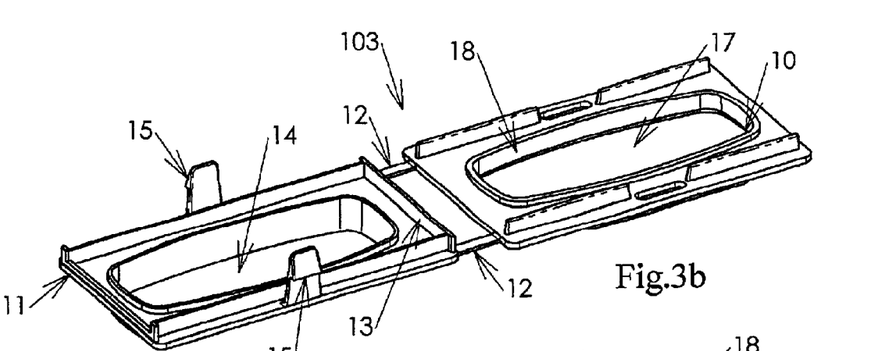
Figure 3C:
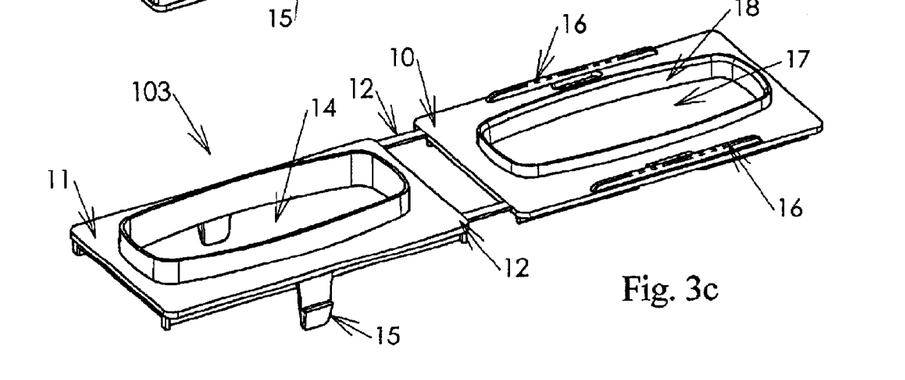
Figure 3D:
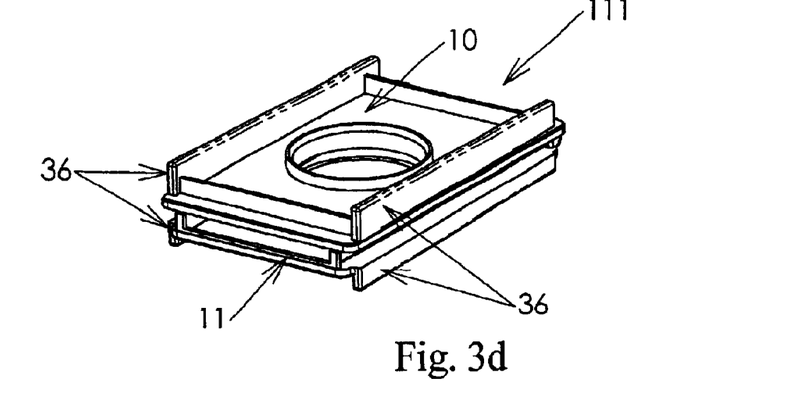
Figure 3E:
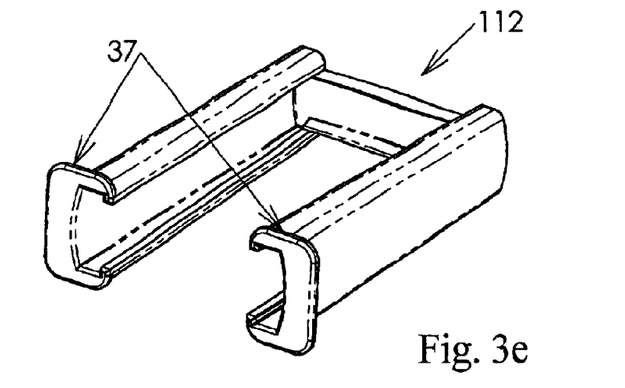
Figure 3F:
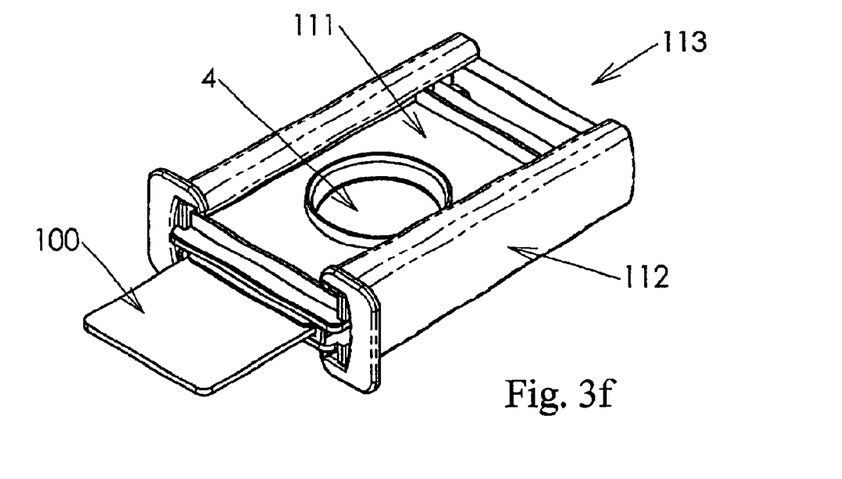

The filter slide (101) is clamped in the Slide Holder (103) (FIGS. 3a–c). The Slide Holder is molded from an appropriate material such as polypropylene or polyethylene. There is a first member (10) and a second member (11) connected at the rear by a living hinge (12) such that the first and second members can be separated from each other yet remain attached. When the Filter Slide (101) is inserted into the second member (11) until it abuts the rear wall (13) of the second member, the aperture (3) of the Filter Slide (101) is aligned with the aperture (14) in the second member of the Slide Holder. When the first member (10) is closed over the second member (11), the spring locks (15) on the second member pass through spaces in the first member and engage the latches (16) on the first member, thereby aligning the aperture (17) in the first member with the apertures of the slide (3) and second member (14), while at the same time clamping the filter slide securely between the first member (10) and the second member (11) and creating a seal between the filter (4) and the first member (10) such that any fluids applied to the top of the filter shall pass through the filter with no alternative fluid paths to the bottom side of the filter. The filter slide may be clamped securely to a Slide Holder that does not contain an integral latching mechanism with the use of an external clamping fixture such as a spring-loaded clamp with fingers extending over the periphery of the Slide Holder. One embodiment that is here illustrated comprises a Slide Holder with no latches FIG. 3D (111) and a set of four locking rails (36) disposed longitudinally near the edges of the first member (10) and second member (11) of the Slide Holder. A Slide Holder Clamp, FIG. 3E (112 ), slidably engages the locking rails thus clamping the filter slide (100) (not shown in this illustration)securely to the Slide Holder (111) forming a Filtration Unit FIG. 3F (113) which can be used as a single assembly.

Figure 3G:
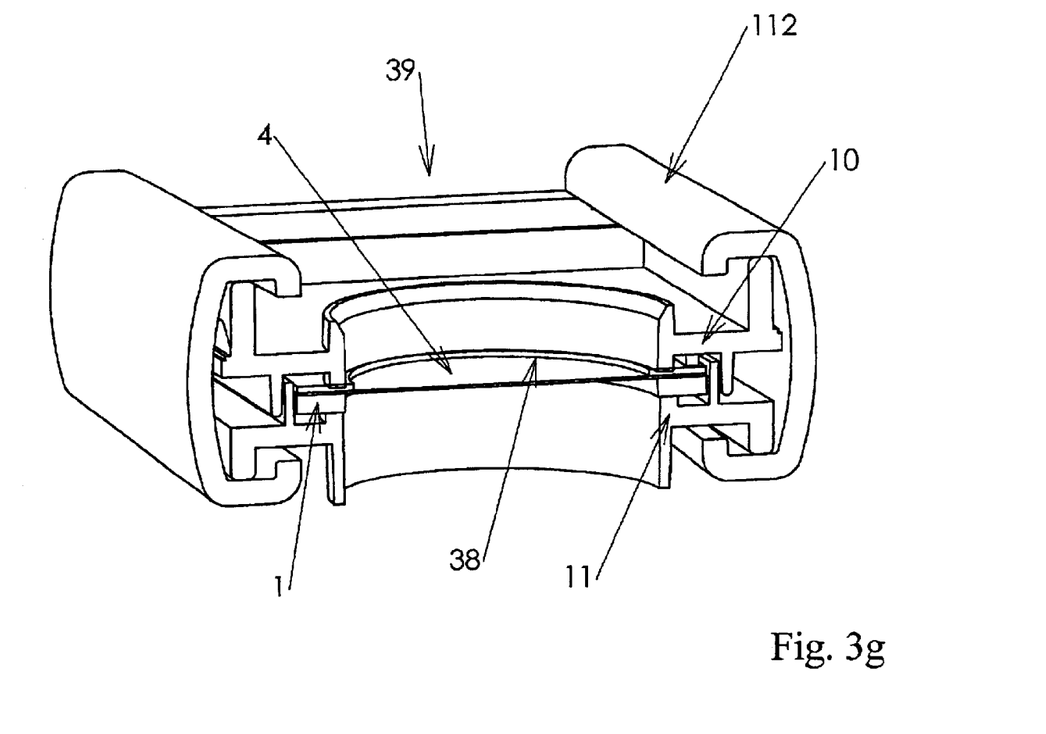
FIG. 3g Filtration Unit cross section combining filter slide, slide holder, slide holder clamp, and sealing gasket.

FIG. 3G illustrates a transverse section through the circular filtration unit (114) at the center of the filter element (4) depicting the Filter Slide (1), with circular membrane (4) attached, clamped between the first member (10) and second member (11) of the slide holder (111), with the sealing gasket (38) interposed on the upstream side (39) between the first member (10) of the slide holder (111) and the filter slide (1).

The Slide Holder, with integral latch or with the Slide Holder clamp, now provides an apparatus for presenting fluids and reagents to either side of the filter membrane through the use of various mating parts and accessories described below.

In order to filter a fluid sample of more than a few milliliters, the funnel (104) (FIG. 4) is press-fit into the aperture (17) in the first member of the Slide Holder, creating a seal between the outer mating wall (19) on the funnel and the inner mating wall (18) of the aperture (17) in the first member (10) of the Slide Holder.

Figure 5:
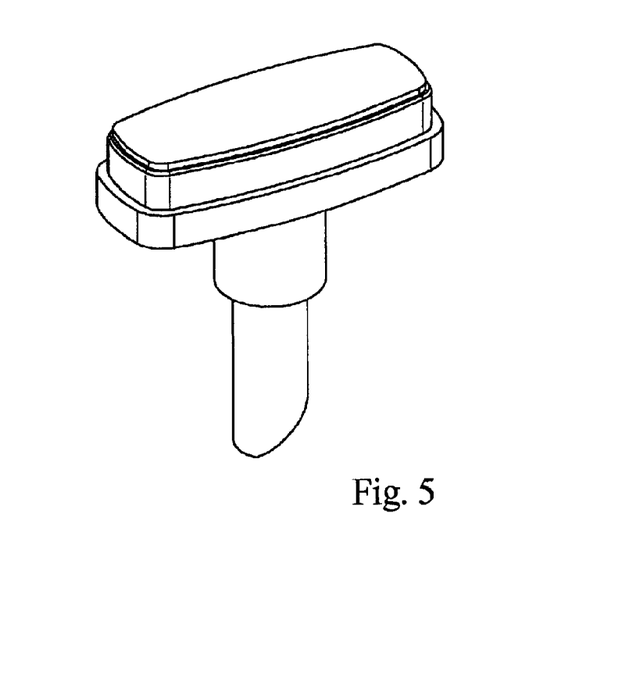
FIG. 5 Vacuum manifold adapter, example

The aperture (14) of the second member (11) of the Slide Holder is fit onto a vacuum source, that illustrated as an adapter (FIG. 5), one end of which fits to a standard vacuum manifold and the other end of which fits inside the bottom aperture (14) of the lower member (11) creating a seal between the inside surface of the aperture (14) and the outside surface of the vacuum adapter, and to support the filter membrane throughout the filtration step. Solution is added to the funnel (104) and a vacuum is applied.

Figure 7:
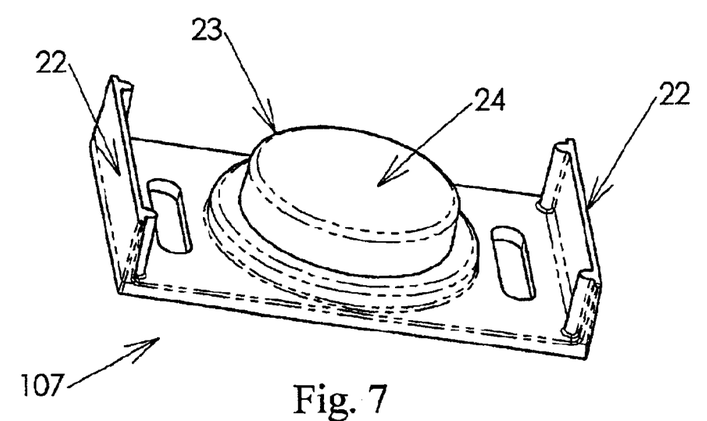
FIG. 7 Top cap for circular filter format and integral latch filter holder

Once the fluid has been filtered, the funnel is removed, and replaced with a top cap (106) (FIG. 6a) to protect the top of the filter membrane and prevent environmental contamination of the filter membrane. The cap is placed over the aperture (17) of the first member (10) such that the ribs (20) on the inner wall (21) of the top cap (FIG. 6b) engage the outer mating wall (25) of the top aperture (17) thus securing the cap to the first member (10) of the Slide Holder without creating a seal between the cap and the first member (10). This feature is important when the invention is to be used for growing microorganisms in an incubator, particularly in that microorganisms are usually incubated "upside down" with the growth medium-imbibed agar or cellulose membrane above the surface on which the microorganisms are growing. The cap of FIG. 6a, when upside down, provides a convenient and stable surface (24) upon which the assembly can rest during incubation. When the circular format filter slide and accessories are used, however, the top of the cap (24) provides an unstable surface to rest on. Thus the cap for the circular filter slide aperture is depicted in FIG. 7, where a pair of feet (22) have been added to the cap portion (23) in order to stabilize the assembly when inverted. If the filtration unit (113) is used, then the circular format top cap (107) can be simplified by retaining only the circular portion, and making the height of the end-flange (37) of the Slide Holder Clamp (112) approximately equal to that of the top surface (24) of the top cap (107 modified), providing together a stable surface to rest upon.

Figure 8A:
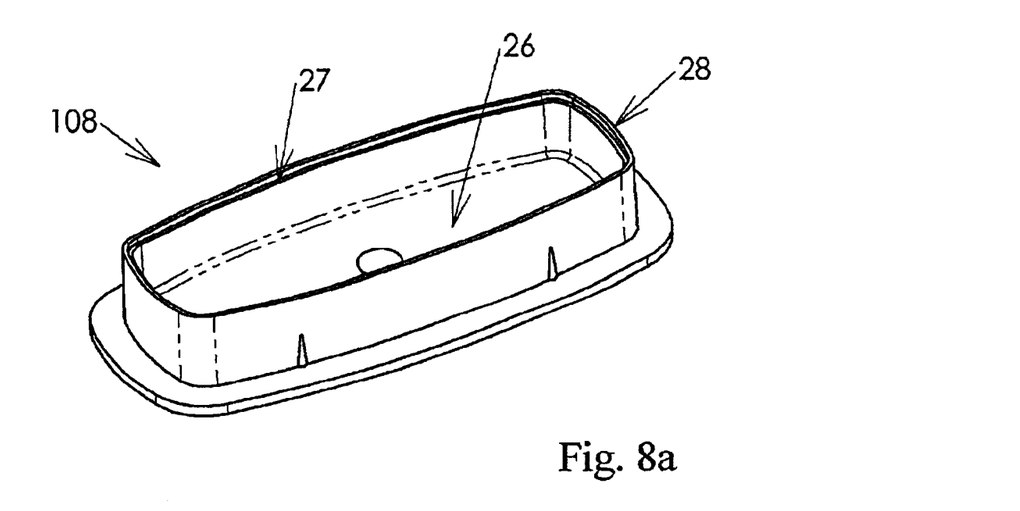
FIG. 8a Reagent Applicator, deep format
Figure 8B:
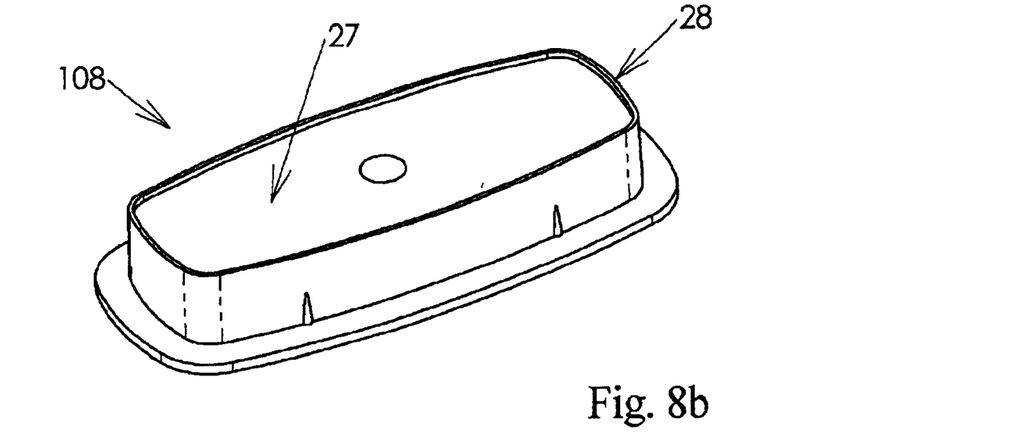
FIG. 8b Reagent Applicator, shallow format

The Filter Slide, with Slide Holder and top cap attached, is removed from the vacuum source, and a Reagent Applicator (108) (FIGS. 8a and b) is inserted from the bottom. These parts are designed such that when the Reagent Applicator reaches a firm "stop" against the top surface (28), reagent, or for the purpose of this example, growth medium is made to come in contact with the bottom of the filter membrane. For agar-based growth medium, the entire cavity (26) is filled with agar. If a cellulose pad, imbibed with liquid growth medium or other reagent, is used, the pad is fit into the shelf (27) near the top of the growth plug and imbibed with reagent or growth medium prior to use. Note that two separate parts can also be fabricated, one with a deep cavity (26) for agar, and one with a shallow cavity (27) for the imbibed pad.

This assembly comprising growth plug, Slide Holder, filter slide, and cap, is inverted and incubated in an incubation oven, usually at 37° C., for a prescribed period of time, usually 4–24 hours. When incubation is complete, the assembly is removed from the incubator, the growth plug is removed, discarded, and replaced with a plug having a cellulose pad impregnated with fixative solution. The assembly is allowed to stand for 5–10 minutes, right side up, at room temperature.

Figure 9:
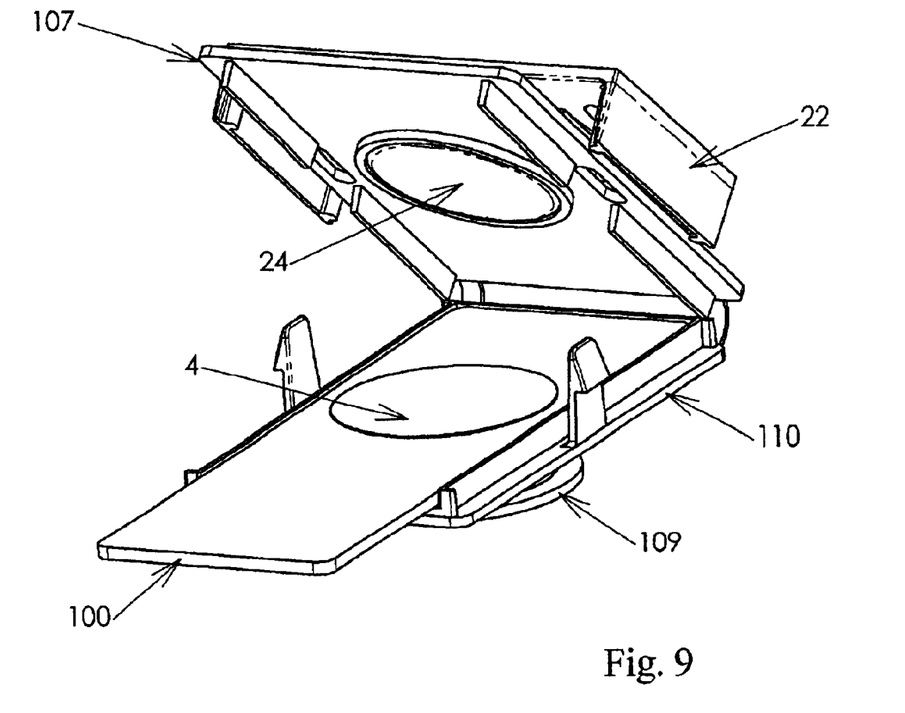
FIG. 9 Filtration Unit assembly with reagent applicator and top cap, circular format FIG. 10 General Process for Sample Preparation and Imaging FIG. 11a Filter Slide with fluorescent bacterial microcolonies, generally elliptical format FIG. 11b Filter Slide with fluorescent bacterial microcolonies, circular format
Figure 10:
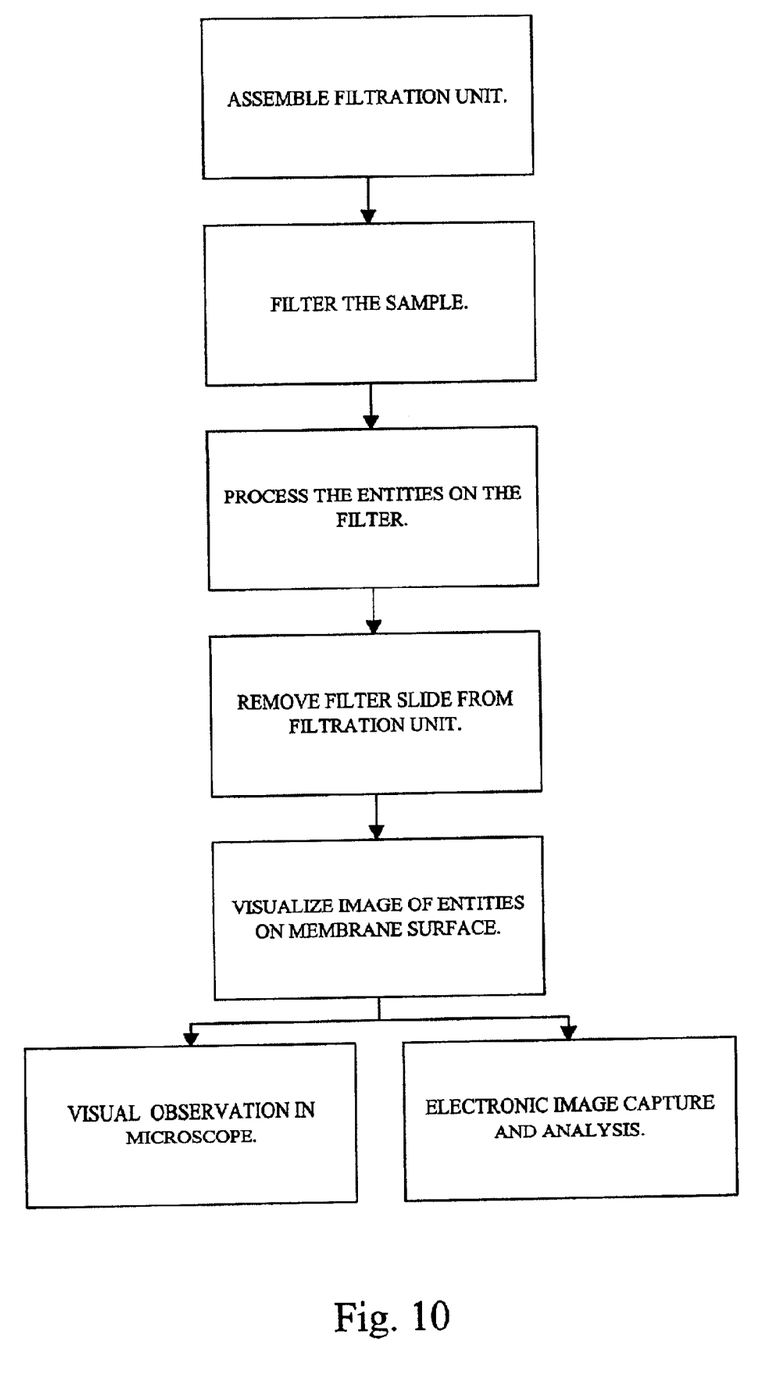

The plug with fixative solution is then removed and replaced with a plug containing no pad. The cap is removed. Hybridization solution is added to the top of the membrane, the cap is inverted and inserted into the top aperture of the first member of the Slide Holder. The top of the cap (24) now forms a thin space over the membrane, distributing the hybridization solution over the entire surface of the membrane. The assembly, illustrated for the circular format membrane in FIG. 9, with the side clamp open to show the interior details, is incubated at an appropriate temperature and time, usually 55° C. for 30 minutes for PNA probes. At the completion of the incubation, the Slide Holder latches are released and the filter slide is removed from the assembly, placed in a standard slide tray, and placed in a wash solution at elevated temperature for 30 minutes after which the filter slide is analyzed in any commercially available imager or scanner, and the bacterial microcolonies are enumerated and the species of microorganism(s) is identified. Throughout this process, the filter is never directly handled and remains protected within the Slide Holder which mediates all processing steps except the final wash. It can then be analyzed by any imager capable of accepting standard microscope slides and compatible with the type of label (e.g. fluorescent, enzyme, chemilununescent) that is attached to the probe being used. In order to facilitate imaging at high magnification (e.g. 5–10 nm spatial resolution), it is preferred that the filter, mounted to the plastic support (FIGS. 1c, 1d), be generally planar, minimizing the need to refocus the imaging device during the visualization process or to develop a more complex optical system (FIG. 10).

EXAMPLE

Serial dilutions of an overnight culture of *E. coli* bacteria were made by adding 40 $\mu$L of a $10^6$ dilution of the bacteria to 2 mL of 1× phosphate-buffered saline (PBS). This dilution was designed to produce 50–100 bacteria per membrane. Bacteria present in the solution were then collected by filtration. A mating funnel (FIG. 4) was attached to the upstream side of a filtration unit, (FIG. 3f) that was comprised of a plastic slide support (round or elliptical aperture, FIGS. 1a, 1b) to which was attached a 0.45 $\mu$m nylon-membrane (Biodyne P/N 14830-0.12, Gibco BRL, Gaithersburg, Md.) (FIGS. 1c, 1d) and that was captured in a slide holder (FIGS. 3a–c). A reagent applicator (FIG. 8a) containing a porous plastic material (Porex P/N 4917, Porex, Inc., Fairburn, Va.) to support the filter slide membrane was inserted into the downstream side of the filtration unit (FIG. 3g) and attached to a vacuum manifold. After filtration, the reagent applicator was removed and replaced with a deep reagent applicator (FIG. 8a) filled with agar. After the agar was contacted with the downstream side of the membrane, the funnel was removed and replaced with a top cap (e.g. FIGS. 6a, 6b). The entire assembly was inverted and placed at 35° C. for 5 hours. After incubation was competed, the assembly was removed from the oven and the agar fixture was removed and replaced with an empty, shallow format reagent applicator (FIG. 8b). To fix the cells, the top cap was removed and 100 $\mu$L of 95% ethanol was pipetted on the upstream side (colony side) of the membrane by aiming the pipette tip at the side of the membrane-filter holder boundary. The ethanol was allowed to "drain" through the membrane. The fixation step was allowed to proceed for 10 minutes.

After fixation, the upstream side of the membrane was probed with Cy3 labeled Eco16S06 PNA oligomer (sequence Cy3-OEE-TCAATGAGCAAAGGT-EE) diluted to a final concentration of 150 nM in Hybridization buffer (containing 10% (w/v) dextran sulfate (Sigma Chemical Co., St. Louis, Mo.), 10 mM NaCl (J. T. Baker), 30% (v/v) formamide (Sigma), 0.1% (w/v) sodium pyrophosphate (Sigma), 0.2% (w/v) polyvinylpyrrolidone (Sigma), 0.2% (w/v) ficoll (Sigma), 5 mM $Na_2$EDTA (Sigma), 4% (v/v) Triton X-100 (Aldrich), 50 mM Tris/HCl pH 7.5). Cy3 is a fluorescent indicator molecule with absorbance maximum at 550 nm and emission maximum at 570 nm (Amersham Life Science, Pittsburgh, Pa.). 200 $\mu$l of the PNA oligomer containing solution was added to the upstream side of the membrane. The top cap was inverted and placed on the upstream through aperture such that the flat portion of the top cap came into contact with the hybridization solution and spread it into a thin sheet across the membrane (colony side) surface. The device was then incubated at 50° C. for 45 minutes. The filter slide was then removed from the filtration unit and placed in a standard microscope slide holder which was incubated, for 20 minutes, in a wash container filled with Wash Buffer (25 mM Tris, pH 7.6, 137 mM NaCl (J. T. Baker), 3 mM KCl (Sigma)) that had been pre-heated to 50° C. At the end of this time the filter slide device was placed in a petri dish in the dark and allowed to dry. Image capture was performed with a Genetics Microsystems (now Affymetrix, Bedford, Mass.) model 418 Confocal Microarray Scanner, 532 nm excitation, 5 micron spatial resolution, gain=19, laser power=20. The Filter Slide was placed on the slide holder of the instrument and then the instrument was used in accordance with the manufacturers instructions to thereby obtain the images of the Filter Slide.

Figures 11A, 11B:
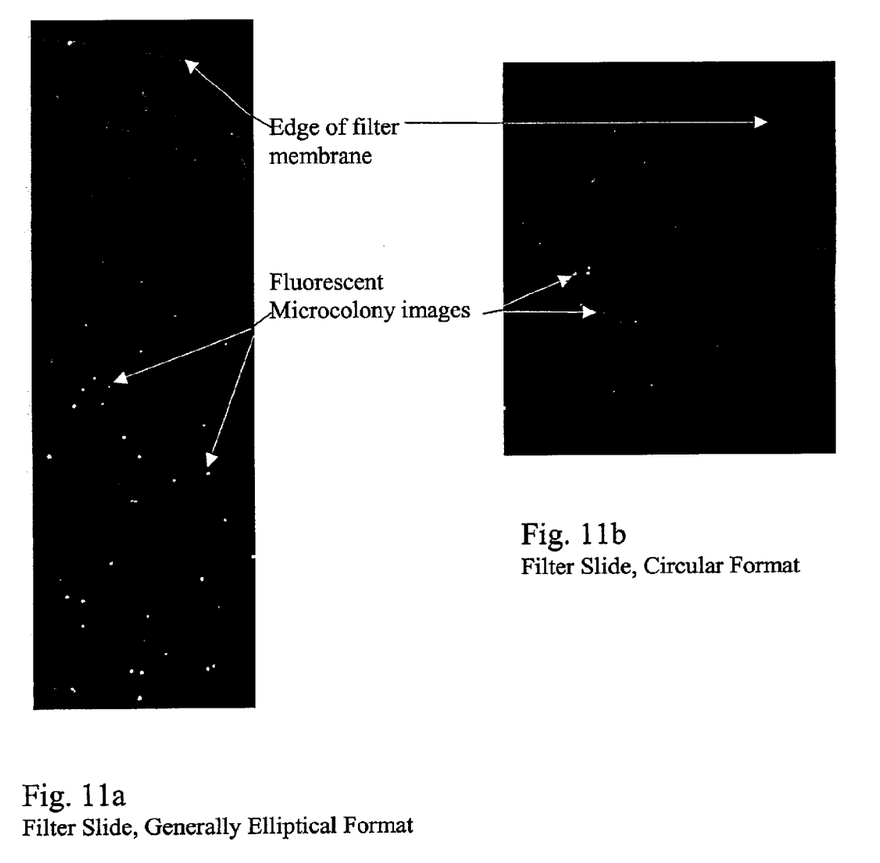

With reference to FIG. 11, the white spots observed on the dark background demonstrate the fluoresence from the cells (microcolonies) that have been stained with the Cy3 labeled PNA probes that are specific for the bacteria in the sample and using the above process. The individual spots are clearly visible above the background and can be counted either manually or by using commercially available image analysis software as previously referenced. The image is so clear and the filter background so low that the boundary between the filter membrane and the slide holder is just visible. Clearly, each microcolony represents growth from single bacteria that were filtered from the original sample. Taken as a whole, it is further clear that this method is useful for the rapid detection, identification and/or enumeration of microscopic entities such as bacteria.

ADVANTAGES OF THE PRESENT INVENTION

Use of the Slide Holder and other components of this invention allows convenient filtration and subsequent processing of a sample with minimal risk of contamination of that sample. After processing, the sample is retained on a low-profile carrier (e.g. the format of a microscope slide) for analysis and archival purposes. The low-profile carrier also can be used to transport the sample through some processing steps, such as washing, where compactness is advantageous and sample isolation is not necessary.

The funnel and Slide Holder can be formed as a single molded part with a frangible region at the base of the funnel portion to allow the funnel portion to be broken away after filtration. Although the Slide Holder is described herein as a molded plastic apparatus, it can be constructed of a durable material for reuse in certain applications where, for example, precision of alignment is important.

The Filter Slide Apparatus can be used independently with processing apparatus that is already in commerce designed to handle microscope slides directly. This feature is particularly evident in the microarray application, where an entire industry has developed to process these arrays that have been deposited on microscope slides.

The Filter Slide in combination with the Slide Holder and the Funnel provide an apparatus and process for filtering a fluid sample such that entities in the sample remain deposited on the Filter Slide. The slide can now be removed and processed as described above.

The Filter Slide in combination with all of the peripheral apparati provide an apparatus and process for the enumeration and identification of bacteria filtered from a fluid sample.

We claim:

1. A method for separation of microscopic entities from a fluid, said method comprising:
   a) providing a filtering apparatus having a microscopic entity filtering element that is supported by a slide support having an aperture therethrough, said slide support having a microscope slide dimensional form factor and, with said filtering element having first and second surfaces and being positioned with respect to said slide support aperture to permit fluid flow through said filtering element;
   b) mounting said filtering apparatus in a slide holder so that both surfaces of the microscopic entity filtering element are exposed;
   c) presenting said filtering element to a fluid that contains microscopic entities in order to capture on said filtering element a plurality of said microscopic entities; and,
   d) utilizing at least a portion of said filtering element containing microscopic entities.

2. The method of claim 1 wherein said microscopic entities are microscopic particles.

3. The method of claim 1 wherein said microscopic entities are microorganisms.

4. The method of claim 1 wherein said microscopic entities are captured by passing said fluid through said microscopic entity filtering element.

5. The method of claim 1 wherein said microscopic entities are captured on one surface of said filtering element.

6. The method of claim 1 wherein said filtering element has a matrix and said microscopic entities are captured in said matrix.

7. The method of claim 1 further comprising the step of exposing said filtering element containing microscopic entities to at least one reagent.

8. The method of claim 7 wherein said first surface of said filtering element containing microscopic entities is exposed to said at least one reagent.

9. The method of claim 7 wherein said second surface of said filtering element containing microscopic entities is exposed to said at least one reagent.

10. The method of claim 7 wherein said second surface of said filtering element containing microscopic entities is exposed to said at least one reagent for reaction at said first surface by percolation through said filtering element.

11. The method of claim 7 wherein said first and second surfaces of said filtering element containing microscopic entities are exposed to said at least one reagent.

12. The method of claim 11 wherein said at least one reagent comprises a series of reagents that are the same reagent.

13. The method of claim 11 wherein said at least one reagent comprises a series of reagents that are different reagents.

14. The method of claim 1 wherein said filtering element is a micro porous structure of organic formulation.

15. The method of claim 1 wherein said filtering element is a micro porous structure of ceramic.

16. The method of claim 1 wherein said filtering element is a micro porous structure of scintered aluminum.

17. The method of claim 7 wherein said filtering element is sequentially exposed to a plurality of reagents.

18. The method of claim 17 wherein at least one surface of said filtering element is sequentially exposed to a plurality of reagents.

19. The method of claim 17 wherein both surfaces of said filtering element are sequentially exposed to pluralities of reagents.

20. A method for separation of microscopic entities from a fluid and imaging of said microscopic entities, said method comprising:
   a) providing a filtering apparatus having a microscopic entity filtering element that is supported by a slide support having an aperture therethrough, said slide support having a microscope slide dimensional form factor and, with said filtering element having first and second surfaces and being positioned with respect to said slide support aperture to permit fluid flow through said filtering element;
   b) mounting said filtering apparatus in a slide holder so that both surfaces of the microscopic entity filtering element are exposed;
   c) presenting said filtering element to a fluid that contains microscopic entities in order to capture on said filtering element a plurality of said microscopic entities; and,
   d) imaging at least a portion of said filtering element containing microscopic entities.

21. A method for separation of microscopic entities from a fluid and imaging of said microscopic entities, said method comprising:
   a) providing a filtering apparatus having a microscopic entity filtering element that is supported by a slide support having an aperture therethrough, said slide support having a microscope slide dimensional form factor and, with said filtering element having first and second surfaces and being positioned with respect to said slide support aperture to permit fluid flow through said filtering element;

b) mounting said filtering apparatus in a slide holder so that both surfaces of the microscopic entity filtering element are exposed;

c) presenting said filtering element to a fluid that contains microscopic entities in order to capture on said filtering element a plurality of said microscopic entities;

d) processing said captured microscopic entities to produce at least one product thereof; and, e) imaging at least a portion of said filtering element containing at least one product of said processed microscopic entities.

22. The method of any of claims 20 or 21 wherein said filtering apparatus is removably mounted in said slide holder.

23. The method of any of claims 20 or 21 wherein said imaging provides a visual image of said at least a portion of said filtering element containing microscopic entities.

24. The method of any of claims 20 or 21 wherein said imaging provides an electronic representation of the image of said at least a portion of said filtering element containing microscopic entities.

25. The method of any of claims 20 or 21 wherein said imaging provides a visual image of said at least a portion of said filtering element containing at least one product of said processed microscopic entities.

26. The method of any of claims 20 or 21 wherein said imaging provides an electronic representation of the image of said at least a portion of said filtering element containing at least one of said processed microscopic entities.

27. An assembly comprising:
a) a slide holder having first and second members each having an aperture therethrough;
b) a filtering apparatus having a microscopic entity filtering element that is supported by a slide support having an aperture therethrough, said slide support having a microscope slide dimensional form factor and, with said filtering element having first and second surfaces and being positioned with respect to said slide support aperture to permit fluid flow through said filtering element, said filtering apparatus being positioned between said first and second members of the slide holder with the filtering element aligned with the first and second member apertures to permit a fluid flow through said filtering element; and,
c) a slide holder clamp that engages said slide holder with the filtering apparatus therein to hold them in a physical relationship to permit fluid flow through said filtering element.

28. An assembly comprising:
a) a slide holder having first and second members each having an aperture therethrough, said first member having at least one male latching post and said second member having at least one corresponding female receiver for said at least one first member male latching post so that the two members can be latched together; and,
b) a filtering apparatus having a microscopic entity filtering element that is supported by a slide support having an aperture therethrough, said slide support having a microscope slide dimensional form factor and, with said filtering element having first and second surfaces and being positioned with respect to said slide support aperture to permit fluid flow through said filtering element, said filtering apparatus being positioned between said first and second members of the slide holder with the filtering element aligned with the first and second member apertures to permit a fluid flow through said filtering element and, with said at least one male latching post and said at least one female receiver in latching engagement.

29. The assembly of any of claims 27 or 28 wherein said slide support aperture and said first and second member apertures have a circular shape.

30. The assembly of any of claims 27 or 28 wherein said slide support aperture and said first and second member apertures have a generally elliptical shape.

31. The assembly of claim 29 further including a funnel having an exit aperture of circular shape that mates with at least one of said first and second member apertures.

32. The assembly of claim 30 further including a funnel having an exit of generally elliptical shape that mates with at least one of said first and second member apertures.

33. The assembly of any of claims 27 or 28 further including a reagent applicator, sealing one of said slide holder member apertures when the applicator is positioned therein.

34. The assembly of any of claims 27 or 28 further including a sealing gasket position between the slide support and the slide holder member that is located on an upstream side of the fluid flow.

35. The method of any of claims 1, 20, or 21 wherein said microscopic entity filtering element is planar.

36. The assembly of any of claims 27 or 28 wherein said microscopic entity filtering element is planar.

* * * * *